US006556868B2

(12) United States Patent
Naritoku et al.

(10) Patent No.: US 6,556,868 B2
(45) Date of Patent: *Apr. 29, 2003

(54) METHODS FOR IMPROVING LEARNING OR MEMORY BY VAGUS NERVE STIMULATION

(75) Inventors: Dean K. Naritoku, Springfield, IL (US); Robert A. Jensen, Carbondale, IL (US); Ronald A. Browning, Carbondale, IL (US); Kevin B. Clark, Murphysboro, IL (US); Douglas C. Smith, Carbondale, IL (US); Reese S. Terry, Jr., Houston, TX (US)

(73) Assignee: The Board of Trustees of Southern Illinois University, Springfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/047,237

(22) Filed: Jan. 14, 2002

(65) Prior Publication Data

US 2002/0099418 A1 Jul. 25, 2002

Related U.S. Application Data

(62) Division of application No. 09/613,368, filed on Jul. 10, 2000, now Pat. No. 6,339,725, which is a division of application No. 08/866,800, filed on May 30, 1997, now Pat. No. 6,104,956.
(60) Provisional application No. 60/018,813, filed on May 31, 1996.

(51) Int. Cl.[7] .................................................. A61N 1/18
(52) U.S. Cl. ...................................................... 607/45
(58) Field of Search ........................... 607/45, 2, 68–76

(56) References Cited

U.S. PATENT DOCUMENTS

| 4,573,481 A | 3/1986 | Bullara |
|---|---|---|
| 4,702,254 A | 10/1987 | Zabara |
| 4,867,164 A | 9/1989 | Zabara |
| 4,920,979 A | 5/1990 | Bullara |
| 4,979,511 A | 12/1990 | Terry, Jr. |
| 4,987,903 A | 1/1991 | Keppel et al. |
| 5,025,807 A | 6/1991 | Zabara |
| 5,154,172 A | 10/1992 | Terry, Jr. et al. |
| 5,186,170 A | 2/1993 | Varrichio et al. |
| 5,215,089 A | 6/1993 | Baker, Jr. |
| 5,222,494 A | 6/1993 | Baker, Jr. |
| 5,235,980 A | 8/1993 | Varrichio et al. |
| 5,237,991 A | 8/1993 | Baker, Jr. et al. |
| 5,251,634 A | 10/1993 | Weinberg |
| 5,269,303 A | 12/1993 | Wernicke et al. |
| 5,304,206 A | 4/1994 | Baker, Jr. et al. |
| 5,351,394 A | 10/1994 | Weinberg |
| 6,104,956 A * | 8/2000 | Naritoku et al. ............... 607/45 |
| 6,339,725 B1 * | 1/2002 | Naritoku et al. ............... 607/45 |

FOREIGN PATENT DOCUMENTS

| GB | 1 347 463 A | 2/1974 |
|---|---|---|
| WO | WO 94/00188 | 1/1994 |

OTHER PUBLICATIONS

K.B. Clark, et al., Post Training Unilateral Vagal Stimulation Enhances Retention Performance in the Rat, Neurobiology of Learning and Memory, May, 1995, pp. 213–216, vol. 63, No. 3.

* cited by examiner

Primary Examiner—Jeffrey R. Jastrzab
(74) Attorney, Agent, or Firm—Senniger, Powers, Leavitt & Roedel

(57) ABSTRACT

Methods of improving memory and learning in humans and animals by vagus nerve stimulation are provided. These methods comprise selecting an appropriate human or animal subject and applying to the subject's vagus nerve an electrical stimulation signal having parameter values effective in modulating the electrical activity of the vagus nerve in a manner so as to modulate the activity of preselected portions of the brain.

17 Claims, 3 Drawing Sheets

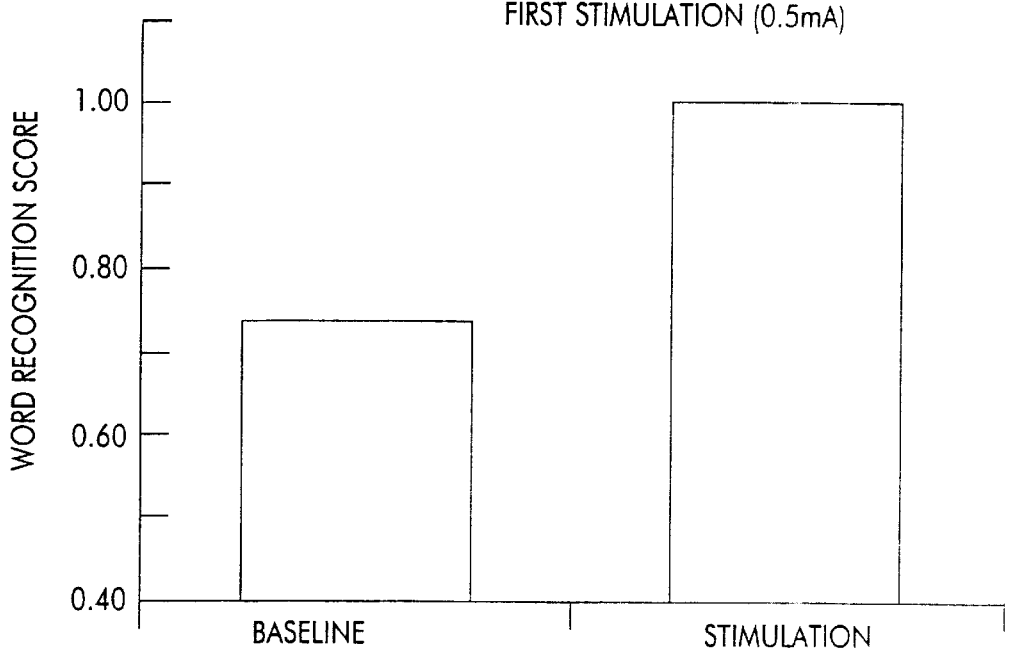
FIG.1 EFFECT OF VAGUS NERVE STIMULATION
FIRST STIMULATION (0.5mA)
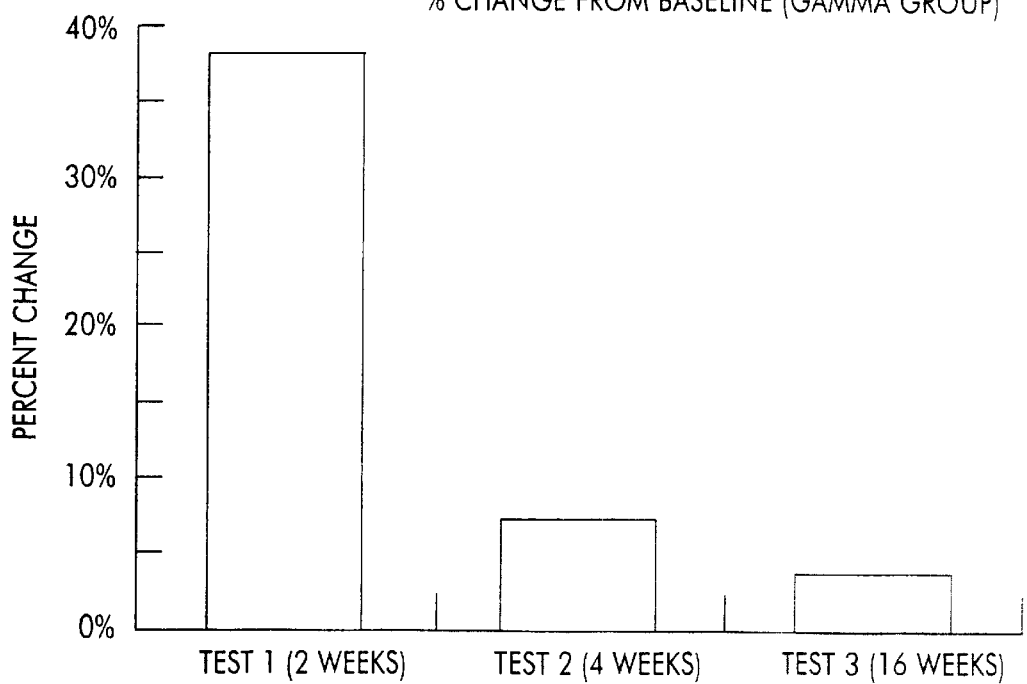
FIG.2 VAGUS NERVE STIMULATION EFFECTS
% CHANGE FROM BASELINE (GAMMA GROUP)

METHODS FOR IMPROVING LEARNING OR MEMORY BY VAGUS NERVE STIMULATION

CROSS REFERENCE TO RELATED APPLICATIONS

This application is a divisional of U.S. patent application Ser. No. 09/613,368, filed Jul. 10, 2000 now U.S. Pat. No. 6,339,725, which is a divisional of U.S. patent application Ser. No. 08/866,800 (now U.S. Pat. No. 6,104,956), filed May 30,1997, which claims priority from U.S. Provisional Patent Application Serial No. 60/018,813, filed May 31, 1996. The texts of U.S. patent application Ser. No. 09/613,368; U.S. patent application Ser. No. 08/866,800 and U.S. Provisional Patent Application Serial No. 60/018,813 are hereby incorporated herein by reference in their entirety.

FIELD OF THE INVENTION

The present invention relates to methods and apparatus for modulating neural plasticity in the nervous system. Neural plasticity includes phenomena such as memory and learning consolidation processes, as well as recovery of function following traumatic brain injury. The methods of the present invention are directed to modulating neural plasticity, improving memory and learning consolidation processes, cognitive processing, and motor and perceptual skills in both normal subjects and subjects suffering from chronic memory impairment, alleviating symptoms and improving outcome in subjects suffering from traumatic brain injury, preventing the development of epilepsy in subjects prone to developing this condition, and treating persistent impairment of consciousness. These methods employ electrical stimulation of the vagus nerve in human or animal subjects via application of modulating electrical signals to the vagus nerve by use of a neurostimulating device.

BACKGROUND OF THE INVENTION

Vagal Afferents and Their Influence on Physiology and Behavior

The vagus nerve comprises both somatic and visceral afferents (inward conducting nerve fibers that convey impulses toward a nerve center such as the brain or spinal cord) and efferents (outward conducting nerve fibers that convey impulses to an effector to stimulate the same and produce activity). The vast majority of vagal nerve fibers are C fibers, and a majority are visceral afferents having cell bodies lying in masses or ganglia in the neck. For the most part, the central projections terminate in the nucleus of the solitary tract, which sends fibers to various regions of the brain such as the hypothalamus, thalamus, and amygdala. Other projections continue to the medial reticular formation of the medulla, the cerebellum, the nucleus cuneatus, and other regions. The solitary nucleus has important pathways to brain regulatory networks, including the serotonergic nuclei and the noradrenergic nuclei. These neurotransmitter systems are crucial for memory, learning, cognitive and sensory/perceptual processing, and motor skills. These neurotransmitters also prevent the development of epilepsy, i.e., they are antiepileptogenic, and are important for the processes that subserve brain recovery following traumatic injury.

The majority of vagus nerve fibers are viscerosensory afferents originating from receptors located in the lungs, aorta, heart, and gastrointestinal tract, and convey, among other things, cardiopulmonary and nocicepive information to various forebrain and brainstem structures (Cechetto, D. F. (1987) *Federation Proceedings* 46:17–23). Three populations of vasal afferents are known to exist: the vastly abundant unmyelinated C fibers involved in pain mediation, and small myelinated B fibers and large A fibers which subserve autonomic reflexes and probably more complex visceroendocrine responses, such as glucose metabolism and fluid homeostasis (Barraco, I. R. A. (1994) *Nucleus of the Solitary Tract*, CRC Press, Boca Raton). Nearly all vagal afferents terminate in the nucleus of the solitary tract (NTS), where the information they carry is first integrated before being divergently projected to each rostral level of the neuroaxis. Because NTS neurons impinge on a number of CNS structures and regions, including the hypothalamus, hippocampus, amygdaloid complex, dorsal raphe nucleus, and mesencephalic reticular formation (Rutecki, P. (1990). *Epilepsia* 31 (Suppl. 2):51–56), an equally large number of cognitive, somatic, and visceral operations can be initiated or coordinated with autonomic information. Thus, as one might expect, neural signals sent via vagal afferents have a profound impact on CNS function that, in turn, influence general behaviors and arousal. For instance, electrical stimulation of the cervical vagus can modify the electrophysiological profile of neocortical, thalamic, and cerebellar neurons. These and other changes in supramedullary circuits are thought to precipitate overt changes in, for example, sleep, feeding behavior, responsiveness to noxious stimuli, and monosynaptic muscular reflexes (Rutecki, supra).

Vagus Nerve Stimulation and the Brain

Vagus nerve stimulation has been shown to cause activation of several parts of the brain that are specifically involved in cognitive processing, memory, learning, sensory and motor processing, and affects regions of the brain that are prone to developing epilepsy or which regulate the development of epilepsy (Naritoku et al. (1995) In Ashley et al., Eds., *Traumatic Brain Injury Rehabilitation*, CRC Press, Boca Raton, pp. 43–65). These studies demonstrate that vagus nerve stimulation activates the amygdala and cingulate cortex, which are involved in learning and cognitive processing. Such stimulation also activates several thalamic nuclei which serve relay functions. In addition, it activates several sensory nuclei, including the auditory, visual, and somatic sensory systems. Finally, vagus nerve stimulation activates monoaminergic nuclei, especially the locus ceruleus and A5 groups, which provide norepinephrine to the brain. Monoamines are crucial for both learning and memory, and for preventing the development of epilepsy (Jobe et al. (1981) *Biochem. Pharmacol.* 30:3137–3144).

Modulation of Memory by Arousal

Both anecdotal and scientific reports have long suggested that some memories are remembered far more distinctly than others when those memories were stored at the time of a significant emotional or stressful life event. This appears to be an important memory mechanism by which the brain selectively enhances the storage and retrievability of more important memories, while minimizing interference from those that are comparatively inconsequential. The research to date indicates that the storage of permanent memories is susceptible to enhancing or disrupting influences shortly after an initial exposure to salient information (McGaugh, J. L. (1989) *Annual Review of Neuroscience* 12:255–287; McGaugh, J. L. (1990) *Psychological Science* 1:15–25; Squire, L. R. (1987) *Memory and Brain*, Oxford University Press, New York). In clinical and animal studies, improved retention can be produced by a wide variety of treatments, including the peripheral administration of certain hormones, neuromodulators, and stimulant drugs, such as amphetamine. One factor which seems to be common to those agents that enhance memory is that most are related in some way to arousal.

Arousal is associated with the release of adrenal catecholamines and numerous other substances such as the pituitary hormones ACTH and vasopressin. Peripheral administration of these substances has consistently been shown to modulate memory in a dose- and time-dependent fashion (McGaugh et al. (1989) "Hormonal Modulation of Memory" In Brush et al., Eds., *Psychoendocrinology*, Academic Press, New York). For instance, when moderate doses of epinephrine or its agonists are given shortly after training on a memory task, there is enhancement of retention performance measured some time later (Gold et al. (1977) *Behavioral Biology* 20:197–207). Importantly, many substances that modulate memory when either endogenously released or delivered systemically do not freely cross the blood-brain barrier, and are therefore unlikely to influence memory by direct pharmacological action on the brain. Instead, they appear to activate peripheral receptors that in turn send neural messages to those central nervous system (CNS) structures involved in memory consolidation.

Role of the Vagus Nerve in Mediating Arousal-Induced Memory Modulation

The vagus nerve appears to be at least partially responsible for the observed memory-modulating effects of peripherally-acting agents. Williams et al. ((1991) "Vagal afferents: A possible mechanism for the modulation of memory by peripherally acting agents" In: Frederickson et al., Eds., *Neuronal control of bodily function, basic and clinical aspects: Vol. 6., Peripheral signaling of the brain: Role in neuralimmune interactions, learning and memory*, Hogrefe and Huber, Toronto, pp. 467–472) and Williams et al. ((1993) *Physiology and Behavior* 54:659–663) demonstrated that severing the vagus nerve below the level of the diaphragm attenuated the memory-enhancing effects of 4-OH amphetamine, an amphetamine derivative that does not freely enter the CNS, as well as the memory-impairing effects of peripherally-administered Leu-enkephalin. Similar attenuation has also been demonstrated with respect to the memory-modulating capacity of cholecystokinin (Flood et al. (1987) *Science* 234:832–834).

Clinical Measurements of Memory Modulation Induced by Arousal

Arousal has also been demonstrated to affect memory performance in humans. Nielson et al. ((1996) *Neurobiology of Learning and Memory* 66:133–142) studied the effects of muscle-tension-induced arousal on memory storage and later retention performance. In that study, a moderate level of muscle-tension-induced arousal was produced by having subjects, young college students, squeeze a hand dynamometer at various times during or following presentation of one practice and four 20-item word lists presented as slides (one every 5 sec.). Thus, each subject participated in four arousal conditions: no muscle tension; muscle tension (100 sec.) during learning of the list (encoding); muscle tension during the 100-sec. memory consolidation interval (storage); and muscle tension (100 sec.) during the immediate recall of the words (retrieval). List order remained the same for all subjects, but the order of arousal conditions was counterbalanced. A final recognition test was given 5 min. after completion of all lists. The results demonstrated that muscle-tension-induced arousal during the memory consolidation interval significantly enhanced final recognition performance.

In another phase of this investigation, subjects were given a series of two practice and twelve 200-word paragraphs to read. Half of the test paragraphs contained highlighted words. Immediately following completion of each paragraph, two questions (one factual and one logical-inferential) were asked about the content of that paragraph. In addition, for the paragraphs containing highlighted words, subjects were asked to recall as many of the highlighted words as they could. For the muscle-tension arousal paragraphs, immediately after the paragraph was completed, the subject was handed the hand dynamometer and asked to squeeze it during the answering of the questions and the recalling of highlighted words. Following completion of the final paragraph and all questions, a final recognition test of all highlighted words was given. The results indicated significant enhancement of retention performance for the muscle-tension arousal paragraphs compared to the no-tension paragraphs, indicating that arousal can enhance memory storage in a working-memory task.

This experiment was replicated using elderly subjects (Nielson et al. (1994) *Behavioral and Neural Biology* 62:190–200). In this experiment, there were 22 normotensive elderly subjects, 21 elderly subjects taking either calcium-channel blockers or angiotensin-converting enzyme inhibitors to control hypertension, and 21 elderly subjects taking beta-blocker antihypertensive medications. The normotensive elderly subjects and those taking non-beta-blocker medications all showed enhanced long-term memory performance as a result of muscle-tension-induced arousal. However, those subjects chronically taking beta-receptor-antagonist medications showed no enhancement of retention performance. These findings suggest that when arousal occurs, there is an enhanced release of adrenal catecholamines (epinephrine and norepinephrine), and that these substances activate peripheral receptors that send neural messages to the brain to modulate memory storage processes. When these receptors are antagonized by beta-blocker-type antihypertensive medications, the normal processes of memory modulation are impaired. Since epinephrine and norepinephrine do not freely cross the blood-brain barrier, their release by arousal likely modulates memory by causing the transmission of neural messages to the brain, possibly via the vagus nerve pathway. Therefore, antagonizing peripheral beta receptors by beta-blocker-type antihypertensive medications prevented the initiation of these messages by the receptors, thus effectively attenuating the normally occurring modulation of memory storage processes by arousal.

Possible Role of Specific Central Serotonergic and Noradrenergic Pathways in the Modulation of Memory by Vagus Nerve Stimulation The dorsal raphe nucleus is one of two monoaminergic brainstem nuclei, the other being the locus coeruleus, that receives indirect input from vagal afferents. Both nuclei then project that information to various other brain structures implicated in learning and memory processes, such as the amygdaloid complex, hippocampus, and mesencephalic reticular formation (Vertes et al. ( 1994) *Journal of Comparative Neurology* 340:11–26). Thus, the dorsal raphe nucleus and locus coeruleus are well suited to regulate the memory-modulating effects of autonomic arousal. In addition, the dorsal raphe nucleus interacts with the amygdaloid complex to produce conditioned fear responses to inescapable shock and in learned-helplessness paradigms (Maier et al. (1993) *Behavioral Neuroscience* 107:377–788). Elevations in the release of serotonin by the dorsal raphe nucleus also reportedly increase anxiety (Iversen (1984) *Neuropharmacology* 23:1553–1560). It is therefore possible that changes in autonomic activity and arousal are reflected in alterations of dorsal raphe nucleus activity and the subsequent release of serotonin onto neurons found in the amygdaloid complex. It is therefore possible that changes in autonomic activity and arousal are transmitted to the brain via the vagus nerve and are reflected in alterations in the activity of neurons in the dorsal raphe nucleus and the subsequent release of serotonin onto neurons of the amygdaloid complex, a brain structure well-known to be involved in the modulation of learning and memory.

Noradrenergic systems are also known to modulate memory consolidation and amygdaloid complex activity (c f. McGaugh (1989) *Annual Review of Neuroscience* 12:255–287); however, Holdefer et al. ((1987) *Brain Research* 417:108–117) demonstrated that locus coeruleus-maintained discharge does not correlate with the memory modulation produced by peripherally-injected 4-OH amphetamine, D-amphetamine, or epinephrine. Although the locus coeruleus receives indirect vagal input, it also receives serotonergic projections from the dorsal raphe nucleus. Consequently, dorsal raphe nucleus activity might suppress the responsiveness of locus coeruleus neurons to autonomic stimulation, thereby increasing serotonergic control over the amygdaloid complex and other brain areas during the memory consolidation period. This hypothesis is supported directly by studies of Naritoku et al.((1995) In Ashley et al., Eds., *Traumatic Brain Injury Rehabilitation*, CRC Press, Boca Raton, pp. 43–65), which demonstrated activation of the locus ceruleus and A5 nuclei, which are noradrenergic neurons. Preliminary evidence of Krahl et al. ((1994) *Society for Neuroscience Abstracts* 20:1453) also indicates that cells found in the dorsal locus coeruleus respond differentially to those found in either the ventral locus coeruleus or subcoeruleus following vagus nerve stimulation.

Modulation of Memory by Peripherally-Acting Substances

Previous research has suggested that the vagus nerve plays a role in the modulation of learning and memory brought about by peripherally-acting substances such as catecholamines, peptides, etc. (Williams et al. (1991) In Frederickson et al., Eds., *Neuronal Control of Bodily Function, Basic and Clinical Aspects: Volume 6, Peripheral Signaling of the Brain: Role in Neural-Immune Interactions, Learning and Memory*, Hogrefe & Huber, Toronto, pp. 467–472; Williams et al. (1993) *Physiology and Behavior* 54:659–663; Flood et al. (1987) *Science* 234:832–834). This work suggests that the vagus nerve may represent a neural pathway through which such substances alter retention performance. However, the effects of direct electrical activation of the vagus nerve on learning and memory in humans have not been previously studied.

Chemical vs. Direct Electrical Stimulation of the Vagus Nerve

1. Chemical Stimulation

Hormonal or chemical (drug) agents function by interacting with specific receptor proteins on neurons. When activated by a neurotransmitter, hormone, or drug, these receptor proteins then either: 1) cause a chemical change in the cell, which indirectly causes ion channels embedded in the membrane to either open or close, thus causing a change in the electrical potential of the cell, or 2) directly cause the opening of ion channels, which causes a change in the electrical potential of the cell. This change in electrical potential then triggers electrical events that are conducted to the brain by the axons of sensory nerves such as those contained in the vagus.

Neural activity is constantly being controlled by the endogenous release of hormones, neurotransmitters, and neuromodulators. However, for therapeutic or experimental purposes, changes in neural activity can also be produced by the administration of chemical or hormonal agents (drugs). When administered exogenously, these agents interact with specific proteins either inside neurons or on the surface of the cell membrane to alter cell function. Chemical agents can stimulate the release of a neurotransmitter or family of neurotransmitters, block the release of neurotransmitters, block enzymatic breakdown of neurotransmitters, block reuptake of neurotransmitters, or produce any of a wide variety of other effects that alter nervous system functioning. A chemical agent can act directly to alter central nervous system functioning or it can act indirectly so that the effects of the drug are carried by neural messages to the brain. A number of chemical/hormonal agents such as epinephrine, amphetamine, ACTH, vasopressin, pentylene tetrazol, and hormone analogs all have been shown to modulate memory. Some act by directly stimulating brain structures. Others stimulate specific peripheral receptors.

2. Electrical Stimulation

In contrast, electrical stimulation of a nerve involves the direct depolarization of axons. When electrical current passes through an electrode placed in close proximity to a nerve, the axons are depolarized, and electrical signals travel along the nerve fibers. The intensity of stimulation will determine what portion of the axons are activated. A low-intensity stimulation will activate those axons that are most sensitive, i.e., those having the lowest threshold for the generation of action potentials. A more intense stimulus will activate a greater percentage of the axons.

Electrical stimulation of neural tissue involves the placement of electrodes inside or near nerve pathways or central nervous system structures. Functional nerve stimulation is a term often used to describe the application of electrical stimulation to nerve pathways in the peripheral nervous system. The term neural prostheses describes applications of nerve stimulation in which the electrical stimulation is used to replace or augment neural functions which have been damaged in some way. One of the earliest and most successful applications of electrical stimulation was the development of the cardiac pacemaker. More recent applications include the electrical stimulation of the auditory nerve to produce synthetic hearing in deaf patients, and the enhancement of breathing in patients with high-level spinal cord injury by stimulation of the phrenic nerve to produce contractions of diaphragm muscles. Recently, electrical stimulation of the vagus nerve is being used to attenuate epileptic seizures.

The basis of the effects of electrical stimulation of neural tissue comes from the observation that action potentials can be propagated by applying a rapidly changing electric field near excitable tissue such as nerve or muscle tissue. In this case, the electrical stimulation, when passed through an electrode placed in close proximity to a nerve, artificially depolarizes the cell membrane which contains ion channels capable of producing action potentials. Normally, such action potentials are initiated by the depolarization of a postsynaptic membrane. However, in the case of electrical stimulation, the action potentials are propagated from the point of stimulation along the axon to the intended target cells (orthodromic conduction). However, action potentials also travel from the point of nerve stimulation in the opposite direction as well (antidromic conduction).

Gold and his co-workers have demonstrated that administration of glucose to rats or humans following a learning experience enhances later retention performance (Gold, P. E. (1986) *Behavioral and Neural Biology* 45:342–349; Manning et al. (1993) *Neurobiology of Aging* 14:523–528). Gold has suggested that vagus nerve stimulation may activate descending efferent vagus pathways which directly and indirectly stimulate the liver to release glucose into the systemic circulation. This increased plasma glucose has been postulated to serve as a second messenger to modulate the storage of memories. However, the present investigators recently demonstrated in rats that blocking descending vagus nerve pathways by a topical application of the local anesthetic lidocaine to the nerve did not attenuate memory enhancement produced by vagus nerve stimulation (Clark, K. B., Smith, D. C., Hassert, D. L., Browning, R. B., Naritoku, D. K., and Jensen, R. A. (submitted for publication)). Posttraining electrical stimulation of vagal afferents with concomitant efferent inactivation enhances memory storage processes in the rat (*Society for Neuroscience Abstracts*, 22). These results clearly indicate that the ascending neural messages resulting from vagus nerve stimulation are the active agent mediating the observed enhancement in memory storage processes.

Few experiments in contemporary neuroscience research employ direct nerve tract stimulation to alter global aspects of behavior such as the storage of memories. Most researchers attempt to alter memory and/or behavior by either administering a drug that activates specific neural systems or by electrically stimulating specific groups of neurons in the central nervous system. Thus, the present inventors' discovery of vagus nerve stimulated enhancement of particular neural processes as disclosed herein is novel. In this case, stimulation of the vagus nerve results in the activation of a variety of processes in the brain that result in changes in brain function. It is likely that only some of these processes are related to the modulation of memory storage and that this stimulation also modulates other changes or plastic processes in the brain as well. That direct vagus nerve stimulation influences plastic processes related to brain development or the recovery of function from brain injury is a very good possibility given the already demonstrated effect on one major form of neural plasticity, i.e., memory storage.

Modulation of Memory in Rats by Electrical Stimulation of the Vagus Nerve

Jensen and co-workers (Clark, K. B., Krahl, S. E., Smith, D. C., and Jensen, R. A. (1994) *Society for Neuroscience Abstracts* 20: 802; Clark, K. B., Krahl, S. E., Smith, D. C., and Jensen, R. A. *Neurobiology of Learning and Memory* 63:213–216) demonstrated that direct electrical stimulation of the vagus nerve at a particular intensity (0.4 mA) and frequency (20 Hz) administered shortly after a learning experience resulted in a pattern of effects on retention performance similar to that reported following the administration of some drugs that do not freely cross the blood-brain barrier (chemical stimulation of peripheral receptors). In this experiment, vagus nerve stimulation (0.4 mA) given during the memory consolidation interval modulated later retention performance such that stimulated rats showed better memory. Stimulation at either a lower (0.2 mA) or higher (0.8 mA) intensity had no effect on retention.

Whether one could reasonably predict that this effect observed in rats might extrapolate to human beings is doubtful in view of the substantial differences in neuroanatomy and complexity of memory processes between laboratory rodents and humans. The experiments performed in rats were based on a single-trial training task of great simplicity, i.e., an inhibitory avoidance task. In this task, the animals were placed in a runway, one end of which was brightly illuminated, while the other end was darkened. As rats are nocturnal, burrowing animals, they typically move quickly from the lighted end into the darkened end when the door separating the two ends of the runway is opened. A mild electrical footshock was delivered in the darkened end. Immediately thereafter, each animal was removed from the runway and returned to its home cage, where it received either no stimulation or vagal stimulation through chronically implanted cuff electrodes on the left cervical vagus nerve. Retention was tested 24 hours later. Latency to step through into the darkened end was taken as the measure of retention.

In the case of human memory, especially verbal memory, the neural systems involved are much more complex than those involved in the learning of a simple avoidance training task by the rat. Learning of concepts, vocabulary, and procedures by humans is qualitatively and quantitatively different from a rat's learning to avoid the end of a runway where punishment, i.e., a footshock, has occurred. Many human brain structures, such as those that mediate language, for example, do not even exist in the laboratory rat. It is therefore possible that the foregoing phenomenon observed in rats is limited to infrahumans, and it is therefore not reasonably predictable that vagal nerve stimulation modulation of memory in the laboratory rat would generalize to human subjects. The applicability of vagal nerve-stimulated modulation of learning of tasks such as complex verbal tasks has for the first time been demonstrated by the present inventors as disclosed herein.

Uniqueness of Vagus Nerve Stimulation in Modulating Memory

Vagus nerve stimulation is completely unlike other experimental manipulations known to modulate memory. Drugs, hormones, and electrical brain stimulation are all known to alter memory storage processes. For example, administration of adrenal hormones (such as epinephrine) or pituitary hormones (such as ACTH) after a learning experience results in the enhancement of memory in a dose-dependent manner. Very low doses are without effect; intermediate doses tend to improve retention performance; very high doses tend to cause amnesia. These hormonal substances and pharmacological agents are thought to act on memory processes by activating specific receptors in the periphery which, in turn, send neural messages to the brain to either enhance or impair the storage of memories.

In contrast, vagus nerve stimulation directly activates one principal nerve pathway connecting the central nervous system with peripheral structures located in the viscera. In this case, the step of chemically activating receptors in the periphery is avoided. Rather, action potential messages in the nerve are directly triggered by the electrical stimulation. These messages pass along the vagus nerve and activate those brain structures in which the nerve fibers terminate. The result is release of neurotransmitters and activation of still other brain structures. Following this, there are alterations in brain function such as the well-established reduction in epileptic seizures and the recently demonstrated enhancement in CNS plasticity, specifically, facilitation of memory storage processes.

Brain Neural Plasticity

The term "neural plasticity" can be viewed as encompassing those structural alterations in the brain that lead to changes in neural function. Such changes in neural function then lead to changes in behavior or in the capacity for behavior. Learning and memory can be thought of as one common form of neural plasticity. The storage of memories following a learning experience is the result of structural and functional changes that occur in specific groups of neurons. Every time something is learned, there is a change in that organism's nervous system which encodes that new information. Such a change does not necessarily result in an immediate change in behavior; rather, it results in an alteration in behavior potential.

During development of the nervous system both before and after birth, there are profound plastic changes taking place which shape the structure and function of the brain. Before birth, groups of nerve cells form, migrate to their assigned location in the brain, and then make connections with other cells. Following birth, neurons continue to sprout new projections, and these branches expand dramatically in complexity, sometimes extending great distances, and making connections with other cells of the nervous system. This process, another form of neural plasticity, continues at a decreasing rate from the time of birth until adolescence.

Neural plasticity is thought to be moderated by a wide variety of cellular and molecular events, including transcription and translation of DNA, which produces cellular proteins that cause long-term changes in neuronal function. One such signal is thought to be the protein fos, which is produced by neurons under conditions of high activity. This protein signals the transcription of other proteins, and is thought to mediate long-term neuronal changes. It may be induced by several neurotransmitters, including excitatory amino acids and monoamines. Naritoku et al. ((1995) *Epilepsy Research* 22:53–62) demonstrated that fos is induced by stimulation of the vagus nerve in widespread areas of the brain (see FIG. 3), thus demonstrating that vagus nerve stimulation activates many areas in the brain, and furthermore, appears to induce the production of a protein that causes further transcriptional events that may in turn mediate neural plasticity.

Memory and Learning and Their Modulation

It is clear that learning and memory are not unitary processes and that there are different types of memory that are mediated by different brain structures. On one level of analysis, it is possible to distinguish between two broad classes of memories, "explicit" and "implicit." When explicit memory is to be assessed, measures such as recall and recognition are used. These measures depend on the conscious recollection of previously stored information. Recognition performance is generally considered to be among the most sensitive measures of explicit memory. Tests of implicit memory infer learning from the effects that experience or practice has on the subject's performance. For example, prior exposure to words will enhance later performance in recognizing these words when they are flashed very rapidly on a screen or presented as word fragments.

Another distinction between types of memory is that between "procedural" and "declarative" memories. These are typically defined as "knowing how" and "knowing that." Procedural memories include perceptual, cognitive, and motor skills, while declarative memory includes such things as facts, events, and routes between places. Both forms of memory can be modulated by various agents, although declarative memories are more subject to disease-produced amnesia than are procedural memories.

We know from our own every-day experiences that some occurrences or events are remembered clearly while others are remembered poorly or perhaps not at all. This is true of procedural and declarative memories whether assessed implicitly or explicitly. It is well established in laboratory animals that retention can be either impaired or enhanced by experimental treatments such as electrical brain stimulation, the administration of stimulant drugs, or the administration of hormones (McGaugh et al. (1972) *Memory Consolidation,* San Francisco, Albion Publishing Company). What is commonly reported is that retention performance, measured some time after the learning experience, can be modulated by changing the parameters of training or by the administration of chemical stimulation shortly after the time of training. Although the underlying mechanisms that mediate memory modulation are not well understood, it appears that several common principles may mediate differences in the quality of remembering.

One major variable influencing retention performance appears to be level of arousal. Early in the development of the behavioral sciences, the Yerkes-Dodson principle was described (Yerkes et al. (1908) *Journal of Comparative Neurology and Psychology* 18:459–482). This principle is characterized by an inverted U-shaped relationship between the amount of motivation or arousal and the resultant level of behavioral performance. This relationship can be seen between the level of arousal and the effectiveness of memory storage processes. For example, either low or very high levels of arousal produce relatively poor learning and memory. However, an intermediate level of arousal results in relatively good memory for a learning experience (McGaugh, J. L. (1973) *Annual Review of Pharmacology* 13:229–241). A similar curve showing an inverted U-shaped function is seen in the data obtained using laboratory rats and vagus nerve stimulation delivered after training. It is important to note that memory is modulated by post-training treatment. In such an experiment, the learning occurs in a normal state and then after training, the treatment is administered. Thus, the primary effects of the treatment are on the storage of the memory and not on other aspects of the experience such as perception or level of motivation.

Traumatic Brain Injury

Another form of neural plasticity is recovery of function following brain injury. As in the case of memory formation or brain development, in this case too there is a change in the ways that neurons interact with one another. When neurons are lost due to disease or trauma, they are not replaced. Rather, the remaining neurons must adapt to whatever loss occurred by altering their function or functional relationship relative to other neurons. Following injury, neural tissue begins to produce trophic repair factors, such as nerve growth factor and neuron cell adhesion molecules, which retard further degeneration and promote synaptic maintenance and the development of new synaptic connections. However, as the lost cells are not replaced, existing cells must take over some of the functions of the missing cells, i.e., they must "learn" to do something new. In part, recovery of function from brain traumatic damage involves plastic changes that occur in brain structures other than those damaged. Indeed, in many cases, recovery from brain damage represents the taking over by healthy brain regions of the functions of the damaged area. Thus, such recovery can be viewed as the learning of new functions by uninjured brain areas to compensate for the loss of function by other regions. Studies of the effect of vagus nerve stimulation on fos production demonstrate that such stimulation induces transcriptional events that produce proteins which in turn stimulate further cellular transcriptional activity (Hughes et al. (1995) *Pharmacol. Rev.* 47:133–178). Increases in neuronal cellular activity will enhance the recovery of function after traumatic brain injury.

Traumatic brain injury results from a wide variety of causes including, for example, blows to the head from objects; penetrating injuries from missiles, bullets, and shrapnel; falls; skull fractures with resulting penetration by bone pieces; and sudden acceleration or deceleration injuries.

Traumatic brain injury represents a growing medical problem in the United States and elsewhere. It is an extremely costly illness, not only due to the expenses arising from the acute care required, but also due to the costs associated with rehabilitation and any resulting long-term disability. A therapy that would accelerate the recovery process and/or improve outcome would be highly beneficial to afflicted persons. As many as 40% of persons with severe head injury proceed to develop epilepsy, which further impedes functional recovery from traumatic brain injury. In addition, epilepsy itself further limits function in this population. A therapy that prevents the genesis of epilepsy would therefore significantly benefit traumatically brain injured persons.

Memory Disorders

A third form of neural plasticity relates to the treatment of chronic memory disorders. These disorders arise from, for example, Alzheimer's Disease, encephalitis, cerebral palsy, Wernicke-Korsakoff (alcohol-related) syndrome, brain injury, post-temporal lobectomy, Binswanger disease, Parkinson's disease, Pick's disease, stroke, multi-stroke dementia, multiple sclerosis, post arrest hypoxic injury, near drowning, etc.

SUMMARY OF THE INVENTION

As demonstrated in the non-limiting Examples disclosed infra, vagus nerve stimulation employed with the appropriate parameters can improve memory and learning in human and animal subjects. When delivered shortly after a learning experience, vagus nerve stimulation results in the initiation of nerve impulses that travel to those brain structures where the nerve terminates, predominantly the nucleus of the solitary tract. The resultant release of neurotransmitters and activation of cells in the vagus nerve target structures results in the activation of other brain areas including those such as the amygdala and hippocampus that are known to be involved in memory storage and the modulation of memory. The result is facilitated memory storage (consolidation) and improved retention performance when memory is measured at some later time. Vagus nerve stimulation can also be employed in the treatment of human and animal subjects suffering from various forms of brain damage or from traumatic head injury.

It is well known that central nervous system neurons do not regenerate following loss due to disease or injury. Therefore, in order for there to be recovery of function, healthy areas of the brain must "learn" to take over the functions of the damaged area.

As discussed above, both phenomena are manifestations of brain neural plasticity.

Briefly, therefore, the present invention provides a number of methods of influencing various aspects of brain neural plasticity. In one embodiment, the present invention is directed to a method of modulating brain neural plasticity in a human or animal subject. The method comprises applying a stimulating electrical signal to the vagus nerve of a human or animal subject. The stimulating electrical signal being effective to cause a physiological, structural, or neuronal connective alteration in the brain. Neural function in the brain is changed as a consequence of the neuronal connective alteration; thereby changing behavior, or the capacity for behavior, in the human or animal subject.

In another embodiment, the present invention is directed to a method of improving learning or memory in a human or animal subject. The method comprises (a) applying a stimulating electrical signal to the vagus nerve of a human or animal subject, the stimulating electrical signal being effective to enhance memory storage or consolidation processes in the human or animal subject; and (b) improving memory storage or improving the retention of learning experiences, in the human or animal subject.

In another embodiment, the present invention is directed to a method of treating a human or animal subject suffering from a symptom caused by traumatic brain injury or characteristic of traumatic brain injury. The method comprises selecting a human or animal subject suffering from a symptom caused by traumatic brain injury or characteristic of traumatic brain injury; and applying a stimulating electrical signal to the vagus nerve of the human or animal subject, the stimulating electrical signal being effective to alleviate the symptom caused by or characteristic of traumatic brain injury. The method further comprises monitoring the human or animal subject via a member selected from the group consisting of clinical outcome, a clinical test, a laboratory test, and combinations thereof, to determine if the symptom has been alleviated, or if further stimulation of the vagus nerve is required. If required, the vagus nerve is further stimulated and the subject is further monitored as in the preceding steps, until the symptom has been alleviated.

In another embodiment, the present invention is directed to a method of preventing the development of epilepsy in a human or animal subject. The method comprises selecting a human or animal subject predisposed to, or rendered susceptible to, developing epilepsy; and applying a stimulating electrical signal being effective to prevent epilepsy to the vagus nerve of the human or animal subject. The method further comprises monitoring the subject to determine if further stimulation of the vagus nerve is required to prevent epilepsy in the subject; and if required, further stimulating the vagus nerve and monitoring the subject as in the preceding steps, to prevent development of epilepsy in the subject.

In another embodiment, the present invention is directed to a method of treating a human or animal subject suffering from a symptom selected from the group consisting of memory impairment, a learning disorder, impairment of cognitive processing speed, impairment of acquisition of perceptual skills, impairment of acquisition of motor skills, and impairment of perceptual processing. The method comprises selecting a human or animal subject suffering from a symptom selected from the group consisting of memory impairment, a learning disorder, impairment of cognitive processing speed, impairment of acquisition of perceptual skills, impairment of acquisition of motor skills, and impairment of perceptual processing; and applying a stimulating electrical signal to the vagus nerve of the human or animal subject. The electrical signal is characterized as being effective to alleviate the symptom in the human or animal subject. The method further comprises monitoring the human or animal subject via a method selected from the group consisting of a clinical test, a laboratory test, determination of clinical outcome, and combinations thereof, to determine if the symptom has been alleviated, or if further stimulation of the vagus nerve is required to alleviate the symptom; and if required, further stimulating the vagus nerve and monitoring the human or animal subject as in the preceding steps, until the symptom has been alleviated.

In another embodiment, the present invention is directed to a method of treating a human or animal subject suffering from persistent impairment of consciousness. The method comprises selecting a human or animal subject suffering from persistent impairment of consciousness; and applying a stimulating electrical signal to the vagus nerve of the human or animal subject. The stimulating electrical signal is characterized as being effective to alleviate the persistent impairment of consciousness in the human or animal subject. The method further comprises monitoring the human or animal subject via determination of clinical outcome to determine if the persistent impairment of consciousness has been alleviated, or if further stimulation of the vagus nerve is required to alleviate the persistent impairment of consciousness; and if required, further stimulating the vagus nerve and monitoring the human or animal subject as in the preceding steps, until the persistent impairment of consciousness has been alleviated.

Further scope of the applicability of the present invention will become apparent from the detailed description and drawings provided below. However, it should be understood that the detailed description and specific examples, while indicating preferred embodiments of the present invention, are given by way of illustration only since various changes and modifications within the spirit and scope of the invention will become apparent to those skilled in the art from this detailed description.

BRIEF DESCRIPTION OF THE DRAWINGS

The foregoing and other objects, features, and advantages of the present invention will be better understood from the following detailed description taken in conjunction with the accompanying drawings, all of which are given by way of illustration only and which are not limitative of the present invention, in which:

FIG. 1 is a bar graph showing the effect of vagus nerve stimulation given shortly after a learning experience, collapsed across Gamma and Delta Group patients. Eleven subjects silently read paragraphs containing highlighted words. Word recognition performance was enhanced by vagus nerve stimulation delivered during the memory consolidation interval. Stimulation intensity was 0.5 mA, biphasic pulses, 30 Hz. Highlighted words that were paired with vagus nerve stimulation were recognized with greater frequency ($t(9)=2.78, p<0.03$) than baseline control words (not paired with stimulation).

FIG. 2 is a bar graph showing the effect of vagus nerve stimulation at tolerance intensities for the Gamma Group. Subjects were tested 2 weeks, 4 weeks and 16 weeks after implantation of the neurocybernetic prosthesis. Recognition performance of highlighted words following stimulation was compared to baseline (no stimulation). Vagus nerve stiumlation delivered during the memory consolidation interval significantly enhanced retention performance only at Test 1 given 2 weeks after implantation with a 0.5 mA intensity. Stimulation was ramped up to tolerance level after Test 2 and stimulation intensity averaged 1.2 mA on Tests 2 and 3. It is unclear whether the decrement in the magnitude of the effect is due to the increased stimulation intensity or to a reduction in effect with the passage of time.

DETAILED DESCRIPTION OF THE INVENTION

Figure 3:
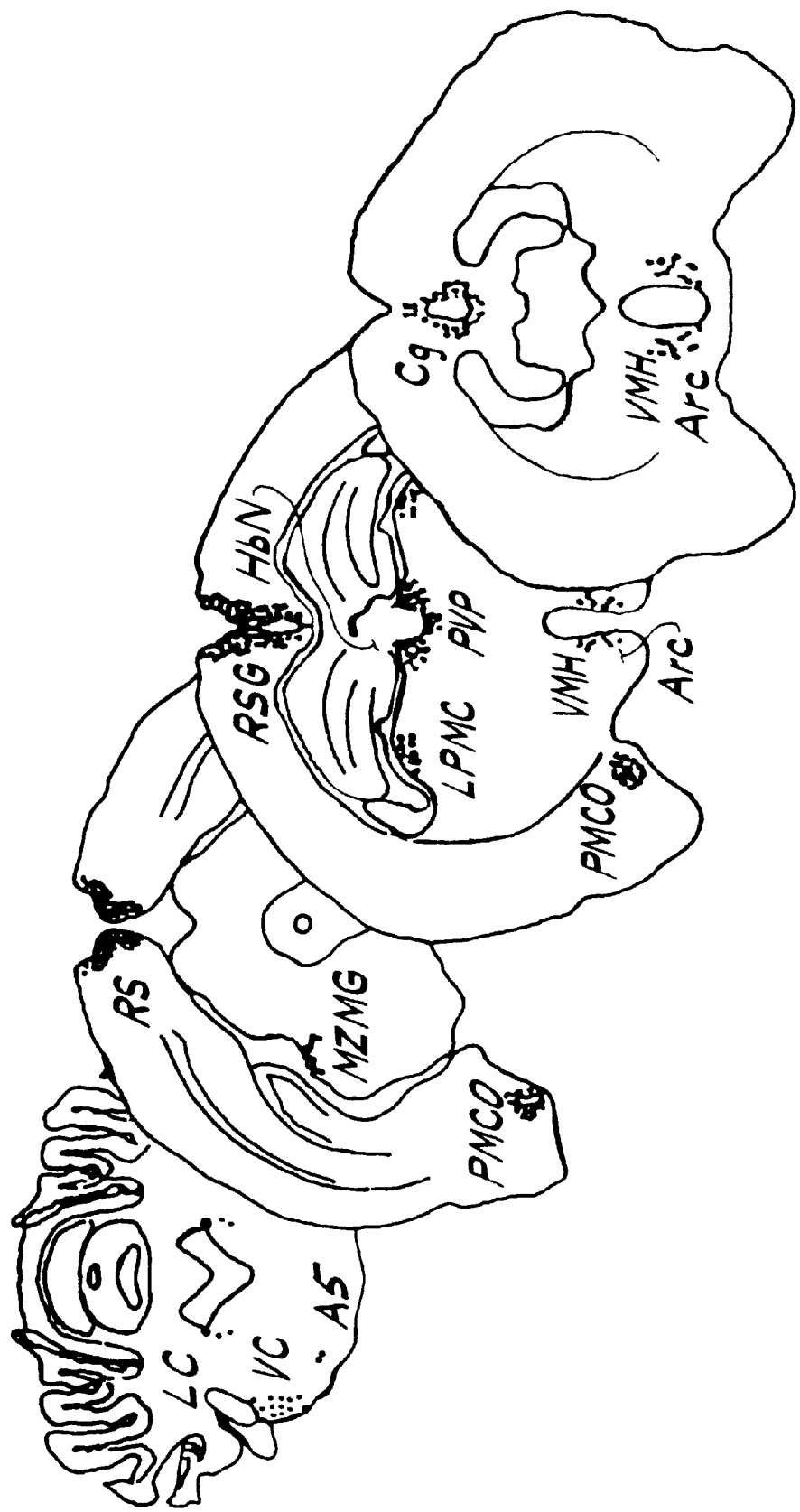
FIG. 3 is a camera lucida drawing of fos immunolabeling in the brain induced by vagus nerve stimulation for three hours (from FIG. 4 of Naritoku et al. (1995) *Epilepsy Research* 22:53–62). The sections are displayed from caudal to rostal levels (left to right), with the relative abundance of labeled nuclei represented by the density of the dots in the drawings. Note the immunolabeling in the cingulate, and retrosplenial cortex, and in the amygdala. In the thalamus, there is labeling in the habenula, lateral posterior nucleus, and marginal zone of the medial geniculate body, and in the hypothalamus there is labeling in the ventromedial and arcuate nuclei. In the brainstem there is immunolabeling in the locus ceruleus, A5 nuclei and cochlear nuclei (Abbreviations: A5=A5 nucleus; Arc=arcuate nucleus; Cg=cingulate cortex; HbN=Habenular nucleus; LC=locus ceruleus; LPMC=Lateral postr thalamic nucleus; MZMG=marginal zone of medial geniculate; PMCO=postr medial cortical amygdalar nucleus; PVP=paraventricular nucleus of thalamus; RS=retrosplenial cortex; RSG=retrosplenial granular cortex; VC=ventral cochlear nucleus; VMH=ventromedial hypothalamic nucleus).

The following detailed description of the present invention is provided to aid those skilled in the art in practicing the same. Even so, the following detailed description should not be construed to unduly limit the present invention as modifications and variations in the embodiments discussed herein may be made by those of ordinary skill in the art without departing from the spirit or scope of the present inventive discovery.

The contents of each of the references cited in the present specification are herein incorporated by reference in their entirety.

Devices for Electrical Stimulation of the Vagus Nerve

The methods of the present invention rely upon modulated electrical stimulation of the vagus nerve. Such electrical stimulation can be achieved by a variety of different methods known in the art. By way of example, such electrical stimulation can be achieved via the use of a neurostimulating device which can be, but does not necessarily have to be, implanted within the subject's body. Forms of neurostimulating devices or accessories therefor that can be employed in the methods disclosed herein are described in U.S. Pat. Nos. 4,573,481; 4,702,254; 4,867,164; 4,920,979; 4,979,511; 5,025,807; 5,154,172; 5,179,950; 5,186,170; 5,215,089; 5,222,494; 5,235,980; 5,237,991; 5,251,634; 5,269,303; 5,304,206; and 5,351,394.

While the reader is referred to the disclosures of these documents for details of various neurostimulating devices useful in the present methods, certain aspects thereof can be summarized as follows for the reader's convenience.

The neurostimulator can utilize a conventional microprocessor and other standard electrical and electronic components, and in the case of an implanted device, communicates with a programmer and/or monitor located externally to the subject's body by asynchronous serial communication for controlling or indicating states of the device. Passwords, handshakes, and parity checks can be employed for data integrity. The neurostimulator also includes means for conserving energy, which is important in any battery operated device, and especially where the device is implanted for medical treatment, and means for providing various safety functions, such as preventing accidental reset of the device.

The stimulus generator can be implanted in the patient's body in a pocket formed by the surgeon just below the skin in the chest in much the same manner as a cardiac pacemaker would be implanted, although a primarily external neurostimulator can also be employed. The neurostimulator also includes implantable stimulating electrodes, together with a lead system for applying the output signal of the stimulus generator to the patient's vagus nerve. Components external to the patient's body include a programming wand for telemetry of parameter changes to the stimulus generator and monitoring signals from the generator, and a computer and associated software for adjustment of parameters and control of communication between the generator, the programming wand, and the computer.

In conjunction with its microprocessor-based logic and control circuitry, the stimulus generator can include a battery or set of batteries which can be of any reliable, long-lasting type conventionally employed for powering implantable medical electronic devices, such as those employed in implantable cardiac pacemakers or defibrillators. In a preferred embodiment of the stimulus generator, the battery can be a single lithium thionyl chloride cell. The terminals of the cell are connected to the input side of a voltage regulator which smoothes the battery output to produce a clean, steady output voltage, and provides enhancement thereof such as voltage multiplication or division if required.

The voltage regulator supplies power to the logic and control section, which includes a microprocessor and controls the programmable functions of the device. Among these programmable functions are output current, output signal frequency, output signal pulse width, output signal on-time, output signal off-time, daily treatment time for continuous or periodic modulation of vagal activity, and output signal-start delay time. Such programmability allows the output signal to be selectively crafted for application to the stimulating electrode set to obtain the desired modulation of vagal activity. Timing signals for the logic and control functions of the generator are provided by a crystal oscillator.

A built-in antenna enables communication between the implanted stimulus generator and the external electronics, including both programming and monitoring devices, to permit the device to receive programming signals for parameter changes, and to transmit telemetry information from and to the programming wand. Once the system is programmed, it can operate continuously at the programmed settings until they are reprogrammed by means of the external computer and the programming wand.

The logic and control section of the stimulus generator controls an output circuit or section which generates the programmed signal levels appropriate for the condition being treated. The output section and its programmed output signal are coupled (directly, capacitively, or inductively) to an electrical connector on the housing of the generator and to a lead assembly connected to the stimulating electrodes. Thus, the programmed output signal of the stimulus generator can be applied to the electrode set implanted on the subject's vagus nerve to modulate vagal activity in the desired manner.

The housing in which the stimulus generator is encased is hermetically sealed and composed of a myaterial such as titanium, which is biologically compatible with the fluids and tissues of the subject's body.

The implanted stimulus generator can be placed in the subject's chest in a cavity formed by the implanting surgeon just below the skin, much as a pacemaker pulse generator would be implanted. A stimulating nerve electrode set is conductively connected to the distal end of an insulated electrically conductive lead assembly attached at its proximal end to a connector. The electrode set can be a bipolar stimulating electrode of the type described in U.S. Pat. No. 4,573,481. The electrode assembly is surgically implanted on the vagus nerve in the patient's neck. The two electrodes are wrapped about the vagus nerve, and the assembly can be secured to the nerve by a spiral anchoring tether such as that disclosed in U.S. Pat. No. 4,979,511. The lead(s) is(are) secured, while retaining the ability to flex with movement of the chest and neck, by a suture connection to nearby tissue.

The stimulus generator can be programmed using a personal computer employing appropriate software and a programming wand. The wand and software permit non-invasive communication with the generator after the latter is implanted, which is useful for both activation and monitoring functions. Programming capabilities should include the ability to modify the adjustable parameters of the stimulus generator and its output signal, to test device diagnostics, and to store and retrieve telemetered data.

Diagnostics testing should be implemented to verify proper operation of the device. The nerve electrodes are capable of indefinite use absent indication of a problem with them observed on such testing.

Although an implantable device for vagus nerve stimulation has been described, it will be apparent to those skilled in the art from the foregoing description that variations and modifications thereof can be readily made. For example, rather than employing a totally implantable **device, one can employ an electronic energization package that is primarily external to the body. Stimulation can be achieved with an RF power device implemented to provide the necessary energy level. The implanted components may be limited to the lead/electrode assembly, a coil, and a DC rectifier. Pulses programmed with the desired parameters would be transmitted through the skin with an RF carrier, and the signal thereafter rectified to regenerate a pulsed signal for application as the stimulus to the vagus nerve to modulate vagal activity. This would virtually eliminate the need for battery changes.

An external stimulus generator can be employed, with leads extending percutaneously to the implanted nerve electrode set.

EXAMPLE 1

Modulation of Brain Neural Plasticity by Vagus Nerve Stimulation

As noted above, the concept of neural plasticity encompasses structural alterations in the brain that lead to changes in neural function. Changes in neural function then lead to changes in behavior, or in the capacity or potential for behavior.

The present inventors have concluded that brain neural plasticity in humans and animals can be modulated by vagus nerve stimulation by the following steps:

(a) applying to the vagus nerve of said human or animal a stimulating electrical signal having parameters sufficient to cause a physiological, structural, or neuronal connective alteration in the brain;

(b) changing neural function in said brain as a consequence of said alteration; and;

(c) changing behavior or the capacity for behavior in said human or animal subject.

Specifically, brain neural plasticity can be modulated as follows.

Apparatus

The neurostimulating device and electrodes can be implanted as described in U.S. Pat. Nos. 5,154,172 and 5,269,303, although any conventional devices known in the art can be employed.

Stimulation Parameters of the Output Signal

The preferred range of stimulation parameters of the output signal of the stimulus generator for modulation of brain neuroplasticity, and the typical value of each parameter of the output signal programmed into the device can be as follows.

The pulse width can be in the range of from about 50 μsec. to about 1,500 μsec., preferably from about 100 μsec. to about 1,000 μsec., more preferably from about 250 μsec. to about 750 μsec., even more preferably from about 400 μsec. to about 750 μsec., and most preferably from about 400 μsec. to about 600 μsec. A pulse width of about 400 μsec. to about 750 μsec. is appropriate when C fiber activation is required or desired. If only A and B fiber activation is required or desired, then a pulse width of about 50 μsec. to about 250 μsec. would be effective. The type of fiber activation can vary between individual patients.

The output current can be in the range of from about 0.1 mA to about 10 mA, more preferably from about 0.1 mA to about 6 mA, most preferably from about 0.1 mA to about 4 mA.

The frequency of the output signal can be in the range of from about 1 Hz to about 75 Hz, more preferably about 5 Hz to about 60 Hz, most preferably from about 10 Hz to about 40 Hz.

The pulses can be monophasic, biphasic, or a combination thereof.

The train duration of the output current can be in the range of from about 1 sec. to about 4 hours, more preferably from about 2.5 sec. to about 2.5 hours, most preferably from about 5 sec. to about 1 hour. The interval between trains can be in the range of from about 1 sec. to about 1 week, more preferably from about 1 sec. to about 1 day, most preferably from about 5 sec. to about 4 hours. Trains can also be supplied on demand.

As will be recognized by those of ordinary skill in the art, any or all of the foregoing vagus nerve stimulation parameters can be titrated clinically to achieve the desired response in a patient.

EXAMPLE 2

Improvement of Memory and Learning by Vagus Nerve Stimulation

Methods and Design

Learning Experiences

The learning experiences to which the methods described herein can be applied include those which are physical, mental, or a combination thereof. As discussed above, learning and memory, one form of neural plasticity, can take many forms. Most commonly, memories are classified as being either procedural or declarative. Further, there are a number of different aspects to each kind of memory. Procedural learning and memory, characterized as knowing how to perform some act, can include the learning and remembering of motor skills, perceptual abilities, and cognitive capabilities. Declarative learning and memory, knowing specific kinds of factual information, can include the knowledge of isolated and connected facts, the events and episodes of one's lifetime, and the routes and pathways of everyday life. As noted supra, each of these kinds of memory is the result of neural plasticity taking place in the brain, and because each can be modulated by peripherally administered chemical agents which do not cross the blood-brain barrier, their mode of action is likely to be through the action of receptors in the viscera that trigger nerve impulses which travel along the vagus nerve to targets in the brain. Hence, the storage of these forms of memory can be modulated by direct stimulation of the vagus nerve, bypassing the need to activate neural receptors in the viscera.

Apparatus

The device and electrodes can be implanted as described in U.S. Pat. Nos. 5,154,172 and 5,269,303, although any comparable device known in the art can be employed.

Stimulation Parameters of the Output Signal

Vagus nerve stimulation subsequent to exposure of a human or animal subject to a learning experience in order to improve learning or memory in that subject can be performed by employing a range of stimulation parameter values of the output signal of the stimulus generator.

The pulse width can be in the range of from about 50 μsec. to about 1,500 μsec., preferably from about 100 μsec. to about 1,000 μsec., more preferably from about 250 μsec. to about 750 μsec., even more preferably from about 400 μsec. to about 750 μsec., and most preferably from about 400 μsec. to about 600 μsec. A pulse width of about 400 μsec. to about 750 μsec. is appropriate when C fiber activation is required or desired. If only A and B fiber activation is required or desired, then a pulse width of about 50 μsec. to about 250 μsec. would be effective. The type of fiber activation can vary between individual patients.

The output current employed for the signal should be of a moderate or intermediate intensity, and can be in the range of from about 0.1 mA to about 10 mA, more preferably from about 0.1 mA to about 6 mA, most preferably from about 0.1 mA to about 4 mA.

The frequency of the output signal can be in the range of from about 1 Hz to about 75 Hz, more preferably about 5 Hz to about 60 Hz, most preferably from about 10 Hz to to about 40 Hz.

The output signal can be monophasic, biphasic, or a combination thereof.

The train duration of the output current can be in the range of from about 1 sec. to about 4 hours, more preferably from about 2.5 sec. to about 2 hours, more preferably from about 5 sec. to about 1 hour, and most preferably about 30 sec. The interval between trains can be in the range of from about 1 sec. to about 60 sec., more preferably from about 2.5 sec. to about 45 sec., most preferably from about 5 sec. to about 30 sec.

The time period after exposure of the human or animal subject to a learning experience in which electrical stimulation of the vagus nerve to improve memory or learning can occur can be in the range of from about 0.01 sec. to about 30 min., more preferably about 0.05 sec. to about 20 min., most preferably about 0.1 sec. to about 15 min. The memory consolidation period in humans typically lasts for 30 minutes after the conclusion of acquisition.

As will be recognized by those of ordinary skill in the art, any or all of the foregoing vagus nerve stimulation parameters can be titrated by routine experimentation to achieve the desired memory enhancement response in a particular subject.

The improved storage of the memory or retention of the learning experience can be observed hours, days, weeks, months, or years after exposing or subjecting a human or animal subject to the learning experience.

Stimuli and Tests for Human Testing

Fourteen narrative paragraphs were used as stimuli in this experiment. Each paragraph was approximately 200 words in length, of appropriate reading level for each subject, and each was typed on a separate page. When presented to the subjects, each paragraph was covered with a cardboard mask that revealed only two lines of text at a time. Subjects were instructed to read at a comfortable pace and to move the mask down the page as the paragraph was read. Subjects were told that they would be questioned about the paragraphs later, and that the mask was being used to prevent reviewing of the material. Two versions of each paragraph were prepared. In one version, seven words were highlighted using a yellow marking pen, and subjects were told that a memory test for these words would follow questions about the paragraph. In the other set of paragraphs, no words were highlighted. Words chosen for highlighting were common nouns, and were distributed equally throughout each paragraph.

In each block of seven paragraphs, the first paragraph was shorter and simpler than the subsequent paragraphs, and served as a warm-up paragraph. Data from these warm-up paragraphs were not included in the analysis. For the six test paragraphs in each block, three "loaded" paragraphs (paragraphs with highlighted words to be remembered) were alternated with three "unloaded" paragraphs (no highlighted words). In addition, in one of the two blocks of paragraphs, stimulation of the vagus nerve occurred, while in the other block, the loaded trials were not associated with vagus nerve stimulation. Whether vagus nerve stimulation occurred in the first or second block of paragraphs was counterbalanced across subjects. The overall design of this experiment is summarized in Table 1.

Following the one-hour rest period, subjects were asked to read a practice paragraph (paragraph X in Table 1) to familiarize them with the use of the cardboard mask during reading. A two-minute rest period followed to allow dissipation of any arousal that might have occurred. Pulse rate and blood pressure were measured at the end of this rest period. The two blocks of six paragraphs each were then administered. There was a five-minute rest period following administration of the first block of paragraphs and the beginning of the second. A warm-up paragraph was also given at the start of the second block of paragraphs. Immediately following completion of each paragraph, pulse rate and blood pressure were recorded and two questions, one factual and one logical-inferential, were asked about the content of that paragraph. In addition, for the loaded paragraphs, subjects were asked to recall the highlighted words following answering of the two questions. For those paragraphs to be paired with vagus-nerve stimulation, immediately after each subject in the Gamma Group com-

TABLE 1

Summary of Experimental Design

| | 1 | 2 | 3 | 4 | 5 | 6 | 7 | Break | 8 | 9 | 10 | 11 | 12 | 13 | 14 |
|---|---|---|---|---|---|---|---|---|---|---|---|---|---|---|---|
| 1 | X | <u>A</u> | B | <u>C</u> | D | <u>E</u> | F | | X | <u>G</u> | H | <u>I</u> | J | <u>K</u> | L |
| 2 | X | <u>B</u> | A | <u>D</u> | C | <u>F</u> | E | | X | <u>H</u> | G | <u>J</u> | I | <u>L</u> | K |
| 3 | X | <u>*A*</u> | B | <u>*C*</u> | D | <u>*E*</u> | F | | X | <u>*G*</u> | H | <u>*I*</u> | J | <u>*K*</u> | L |
| 4 | X | <u>*B*</u> | A | <u>*D*</u> | C | <u>*F*</u> | E | | X | <u>*H*</u> | G | <u>*J*</u> | I | <u>*L*</u> | K |

Letters A–L and X represent the paragraphs of text that were read by the subjects; rows represent the four condition orders. Underlines indicate that highlighted word was present in the paragraphs; italics indicate that stimulation of the vagus nerve was given following reading of the paragraph. Subjects were assigned to an experimental condition via Latin-square rotation.

Procedure for Human Testing

Each subject was given a brief summary of the procedure used in this study at each visit (i.e., visits 2, 5, and 7), and any questions were answered prior to testing. Visit 2 testing served as a pre-implantation baseline consisting of paragraph reading followed by inferential, logical, and retention queries. The procedures for this visit were identical to those discussed below for visits 5 and 7, except that vagus nerve stimulation was not administered. The first series (5 stimulations) of vagus nerve stimulations were given to subjects during visit 5 at an intensity of 0.5 nA with a frequency of 30 Hz (Gamma) or minimal perceptible current (0.25–1 mA) at 1 Hz (Delta). During this time, the reaction of the subject was studied, and appropriate adjustments were made. This enabled each subject to become acquainted with the sensations produced by the stimulation, and helped to minimize possible effects of novelty produced by the sensations associated with stimulation. It is important to eliminate any novelty effects produced by the stimulation.

At that time, during Visit 5, those subjects in the Gamma Group received vagus nerve stimulation at 0.5 mA, 30 Hz. Those in the Delta Group received threshold stimulation to perception (0.25 to 1.0 mA) once every 180 minutes. Following stimulation, a one-hour rest period was given to ensure that any residual effects resulting from these first exposures to the stimulation current were minimized before memory testing procedures began. Ramping procedures began following completion of the memory testing procedure on Visit 5.

pleted reading the paragraph and answering the questions, she/he was given vagus nerve stimulation for 30 sec. Those subjects in the Delta Group received no stimulation.

Following completion of the final paragraph and the answering of questions, an unannounced recognition test of all highlighted words was given. In this test, a list of all 42 highlighted target words was randomly interspersed with 210 distractor words (16.6% target words). The distractor words were highly concrete imageable nouns (Pavio et al. (1968). Concreteness, imagery, and meaningfulness values for 925 nouns. *Journal of Experimental Psychology*, 76, (Suppl), 1–25). Subjects were asked to mark all words which they believed had been previously presented as highlighted words in the paragraphs they had read earlier. When this test was completed, pulse rate and blood pressure were measured and the ramp-up or ramp-down procedure was resumed.

Subjects were again tested during Visit 7 according to the basic procedures described above for Visit 5. This time, however, vagus nerve stimulation given after the reading of half the paragraphs was for the subjects in the Gamma Group at the tolerance intensity that each had been ramped up to. This ranged from 0.75 mA to 1.5 mA. A final test was conducted on Visit 9. This time, subjects in the Gamma Group received vagus nerve stimulation at their individual tolerance intensity (0.75 mA to 1.5 mA), while all subjects in the Delta Group received stimulation at 0.5 mA.

This experimental design enables each subject to establish his/her own baseline against which stimulation effects are measured. Each stimulation group provided a standard of comparison to evaluate the general effects of device implantation and vagus nerve stimulation on memory performance. This is crucial as the pre-implantation baseline measures (Visit 4) rules out changes in performance merely resulting from surgery or the presence of the device. The pre-implantation baseline is not in itself an adequate control for cognitive testing without an additional post-implantation stimulation baseline. This control was provided by paragraph reading followed by no vagus nerve stimulation in each group. Further, this experimental design permits the comparison of the effects of different current intensity levels. One half of the patients (those in the Gamma Group) were treated with 0.5 mA stimulation during Visit 5. The other half of the patients (the Delta Group) received no stimulation at either Visit 5 or Visit 7. On Visit 7, patients in the Gamma Group had their stimulation intensity increased to their own individual tolerance level, not exceeding the ceiling intensity of 1.5 mA. Stimulation intensity is an important factor as the results from laboratory animal studies (Clark et al. (1994) *Society for Neuroscience Abstracts* 20:802; Clark et al. (1995) *Neurobiology of Learning and Memory* 63:213–216) indicate that this is an important parameter. In that case, only 0.4 mA stimulation produced significant enhancement in retention performance. Lastly, if vagus nerve stimulation has a capacity to improve memory or other cognitive functions in humans, it is most likely to do so for those specific events occurring during an interval time-locked to the stimulus. The vagus nerve stimulation stimulus selectively enhances certain information over the milieu of other information during the memory consolidation period. General neuropsychological tests for cognitive and memory performance are not designed to evaluate the time-locked pairing of salient cues (i.e., vagus nerve stimulation-induced arousal) with the acquisition of information. Therefore, any memory-modulating effect would be overlooked or masked (i.e., a lowered mean retention performance) by retention queries for acquired information other than that associated with or time-locked to vagus nerve stimulation. The working memory paradigm described above is, in contrast, sensitive to even subtle vagus nerve stimulation influences on the formation of memories, since retention for words time-locked to vagus nerve stimulation at three different intensities are compared to retention for words time-locked to no vagus nerve stimulation.

Results

Recognition memory performance of eleven patients was analyzed in tests performed on Visits 5, 7, and 9 (two, four, and sixteen weeks postimplantation, respectively). The results are summarized in FIGS. 1 and 2.

Current Intensity at 0.5 mA

FIG. 1 shows the effect of vagus nerve stimulation (0.5 mA, 0.5 ms pulse width, 30 Hz), given shortly after a learning experience, collapsed across Gamma- and Delta-group patients. To counterbalance for time effects, patients (n=5) in the Gamma group received the above mentioned stimulus at Visit 5 while those patients (n=6) in Delta group received the identical stimulation at Visit 9. Each subject read a series of paragraphs, some of which contained highlighted words. In half the trials, reading a paragraph with highlighted words was followed by vagus nerve stimulation. In the other half of the trials, no stimulation was given. Retention performance, measured as recognition of highlighted words, showed that subjects remembered more words from trials that were followed by vagus nerve stimulation than they did in those trials in which no stimulation followed reading of the paragraphs (t(9)=2.78, p<0.025). These data indicate that regardless of the time after device implantation, vagus nerve stimulation at 0.5 mA, when administered after a learning experience, significantly enhanced retention performance of the learned material.

Current Intensity at Subject Tolerance

At Visits 7 and 9, patients in the Gamma group received vagus nerve stimulation at each individual's tolerance intensity (e.g., 0.75 to 1.5 mA). FIG. 2 shows the effect of vagus nerve stimulation at tolerance intensities for the Gamma group. Vagus nerve stimulation given at tolerance intensities (0.75 to 1.5 mA) shortly after a learning experience did not significantly enhance recognition performance (t(9)=0.76, p<0.470). This finding parallels those effects observed for animals in the inventors' laboratory (Clark et al. (1994) *Society for Neuroscience Abstracts* 20:802; Clark et al. *Neurobiology of Learning and Memory* 63:213–216). Animals that received posttraining administration of vagus nerve simulation showed significantly enhanced memory performance at moderate current intensities (i.e. 0.4 mA), but not at the comparatively higher stimulation intensity of 0.8 mA. Such an input-output curve is analogous to the inverted U-shaped dose response curves commonly found for memory modulating drugs. Thus, these findings with human subjects suggest that vagus nerve stimulation produces enhancement of memory storage processes in a manner similar to that of other memory modulatory agents.

EXAMPLE 3

Treatment of Traumatic Brain Injury by Vagus Nerve Stimulation

Vagus nerve stimulation is expected to help sufferers of traumatic brain injury in a number of ways.

First, vagus nerve stimulation induces increased neuronal activity in widespread regions of the brain (Naritoku et al. (1995) *Epilepsy Research* 22:53–62). Such stimulation can ameliorate the problems of brain hypometabolism and decrease in brain activity induced by brain injury, and aid in improving recovery of cognition, motor skills, activities of daily living, and memory.

Secondly, vagus nerve stimulation activates the protein fos in brain neurons (Naritoku et al., supra). Since this protein promotes subsequent transcription and translation of genes, thereby increasing the production of cellular proteins, it enhances brain neural plasticity and thereby contributes to recovery from injury.

Thirdly, vagus nerve stimulation produces widespread increases of monoamines in the brain, including the neurotransmitters serotonin and norepinephrine. Several studies indicate that increases in monoamines are antiepileptogenic, i.e, prevent epilepsy (Gellman et al. (1987) *J. Pharmacol. Exp. Ther.* 241:891–898). While drugs that increase monoamines, such as amphetamines, cause undesired side effects, vagus nerve stimulation represents a means of increasing monoamine transmission without negative side effects.

Next, vagus nerve stimulation will aid in preventing the development of epilepsy. Previous investigations on vagus nerve stimulation have examined the treatment of established chronic epilepsy. The methods disclosed herein are expected to be useful in preventing the development of epilepsy itself. Several types of data support this hypothesis.

First, at least part of the anti-seizure properties of vagus nerve stimulation relates to activation of monoaminergic nuclei. Krahl et al. ((1994) *Society for Neuroscience Abstracts* 20:1453) have demonstrated that inactivation of monoaminergic nuclei reduces the effectiveness of vagus nerve stimulation. Furthermore, the data of Naritoku et al. ((1995) Epilepsy Res. 22:53–62) demonstrate that vagus nerve stimulation activates the A5 and locus ceruleus noradrenergic nuclei.

Secondly, increasing monoaminergic transmission prevents the development of epilepsy in animals (Jobe et al. (1981) *Biochem. Pharmacol.* 30:3137–3144). This property has been termed "antiepileptogenic," as opposed to "antiepileptic" or "anticonvulsant". An antiepileptogenic therapy is distinctly different from antiepileptic or anticonvulsant therapies in that the latter two therapies prevent seizures once epilepsy is established, but do not prevent the development of epilepsy, as do antiepilepto-genic therapies. The effects of vagus nerve stimulation will prevent the processes that cause epilepsy. Specifically, injections of high amounts of monoaminergic drugs such as clonidine block the rate at which epilepsy can be established in animal models using the kindling protocol, which involves direct applications of small amounts of electrical currents to limbic structures (Burchfiel et al. (1989) *Neurosci. Behav. Rev.* 13:289–299; Gellman et al. (1987) *J. Pharmacol. Exp. Ther.* 241:891–898).

Thirdly, increases in serotonin or norepinephrine brought about by drugs such as fluoxetine reduce spontaneous and induced seizures in animals and humans (Jobe et al. (1973) *J. Pharmacol. Exp. Ther.* 184:1–10; Leander (1992) *Epilepsia* 33:573–576; Favale et al. (1995) *Neurology* 45:1926–1927).

Finally, vagus nerve stimulation is expected to improve memory in brain-injured patients. As demonstrated in Example 1, supra, vagus nerve stimulation improves memory function in normal human subjects.

Methods and Design
Types of Brain Injuries Amenable to Treatment by Vagus Nerve Stimulation Vagus nerve stimulation can be used to improve recovery of patients suffering from traumatic brain injury such as that incurred, for example, from blows to the head from various objects; penetrating injuries from missiles, bullets, shrapnel, etc., falls; skull fractures with resulting penetration by bone pieces; sudden acceleration or deceleration injuries; and other causes well known in the art. Exemplary symptoms of such brain injuries include, but are not limited to, impaired level of consciousness, impaired cognition, impaired cognitive processing speed, impaired language, impaired motor activity, impaired memory, impaired motor skills, and impaired sensory skills.

Apparatus

The device and electrodes can be implanted as described in U.S. Pat Nos. 5,154,172 and 5,269,303, although any conventional devices known in the art can be employed.

Stimulation Parameters of the Output Signal

The preferred range of stimulation parameters of the output signal of the stimulus generator for treatment of traumatic brain injury, and the typical value of each parameter of the output signal programmed into the device by the attending physician or therapist, can be as follows.

The pulse width can be in the range of from about 50 $\mu$sec. to about 1,500 $\mu$sec., preferably from about 100 $\mu$sec. to about 1,000 $\mu$sec., more preferably from about 250 $\mu$sec. to about 750 $\mu$sec., even more preferably from about 400 $\mu$sec. to about 750 $\mu$sec., and most preferably from about 400 $\mu$sec. to about 600 $\mu$sec. A pulse width of about 400 $\mu$sec. to about 750 $\mu$sec. is appropriate when C fiber activation is required or desired. If only A and B fiber activation is required or desired, then a pulse width of about 50 $\mu$sec. to about 250 $\mu$sec. would be effective. The type of fiber activation can vary between individual patients.

The output current can be in the range of from about 0.1 mA to about 10 mA, more preferably from about 0.1 mA to about 6 mA, most preferably from about 0.1 mA to about 4 mA.

The frequency of the output signal can be in the range of from about 1 Hz to about 75 Hz, more preferably about 5 Hz to about 60 Hz, most preferably from about 10 Hz to about 40 Hz.

The pulses can be monophasic, biphasic, or a combination thereof.

The train duration of the output current can be in the range of from about 1 sec. to about 4 hours, more preferably from about 2.5 sec. to about 2.5 hours, most preferably from about 5 sec. to about 1 hour. The interval between trains can be in the range of from about 1 sec. to about 1 week, more preferably from about 1 sec. to about 1 day, most preferably from about 5 sec. to about 4 hours. Trains can also be supplied on demand if this is determined to be preferable by the physician or therapist.

The stimulating electrical signal can be applied to the vagus nerve any time after appearance of any of the symptoms noted above, for example, within a time period of from about 1 hour to about 3 months after appearnce of the symptom.

Finally, the duration of the total therapy can vary depending upon the nature and severity of the brain injury, as well as the physical attributes and condition of the patient. Therapy can vary from about one day to as long as continued clinical improvement is obtained or desired, e.g., several months or years to the remainder of the patient's life. The necessity for, or desirability of, further therapy can be determined from results obtained via administering a variety of different clinical or laboratory tests to the patient. Examples of useful clinical tests include tests of activities required for daily living, memory, cognition, motor skills, development of epilepsy, FIM (Functional Index Measurement) scores, and other standardized measurements of functional outcome. Examples of useful laboratory tests include a brain scan, a PET scan, a SPECT scan, an EEG, an evoked potential, monitoring the level of a neurotransmitter such as norepinephrine, serotonin, or dopamine, or metabolites thereof, in the brain, and monitoring the level of a neurotransmitter in spinal fluid.

As will be recognized by those of ordinary skill in the art, any or all of the foregoing vagus nerve stimulation parameters can be titrated clinically to achieve the desired response in a patient.

EXAMPLE 4

Prevention of Epilepsy by Vagus Nerve Stimulation

As noted above in Example 3, various types of data lead to the conclusion that vagus nerve stimulation is expected to be effective in preventing the development of epilepsy. Such therapy is applicable not only in the treatment of patients suffering from traumatic brain injury, but also in preventing the development of epilepsy in other subjects prone to this disorder. This population includes patients predisposed to, or rendered susceptible to, developing epilepsy. These patients include, for example, those suffering from a disease or condition such as traumatic brain injury, post-encephalitic patients, post-stroke patients, and patients having a family history or genetic background predisposing them to developing epilepsy.

Methods and Design
Apparatus

The device and electrodes can be implanted as described in U.S. Pat. Nos. 5,154,172 and 5,269,303, although any conventional devices known in the art can be employed.

Stimulation Parameters of the Output Signal

The preferred range of stimulation parameters of the output signal of the stimulus generator for the prevention of epilepsy, and the typical value of each parameter of the output signal programmed into the device by the attending physician or therapist, can be as follows.

The pulse width can be in the range of from about 50 $\mu$sec. to about 1,500 $\mu$sec., preferably from about 100 $\mu$sec. to about 1,000 μsec., more preferably from about 250 μsec. to about 750 μsec., even more preferably from about 400 μsec. to about 750 μsec., and most preferably from about 400 μsec. to about 600 μsec. A pulse width of about 400 μsec. to about 750 μsec. is appropriate when C fiber activation is required or desired. If only A and B fiber activation is required or desired, then a pulse width of about 50 μsec. to about 250 μsec. would be effective. The type of fiber activation can vary between individual patients.

The output current can be in the range of from about 0.1 mA to about 10 mA, more preferably from about 0.1 mA to about 6 mA, most preferably from about 0.1 mA to about 4 mA.

The frequency of the output signal can be in the range of from about 1 Hz to about 75 Hz, more preferably about 5 Hz to about 60 Hz, most preferably from about 10 Hz to about 40 Hz.

The pulses can be monophasic, biphasic, or a combination thereof.

The train duration of the output current can be in the range of from about 1 sec. to about 4 hours, more preferably from about 2.5 sec. to about 2.5 hours, most preferably from about 5 sec. to about 1 hour. The interval between trains can be in the range of from about 1 sec. to about 1 week, more preferably from about 1 sec. to about 1 day, most preferably from about 5 sec. to about 4 hours. Trains can also be supplied on demand if this is determined to be preferable by the physician or therapist.

Finally, the duration of the total therapy can vary depending upon the nature and severity of the underlying disorder or condition, as well as the physical attributes and condition of the patient. Therapy can vary from about one day or one year to as long as continued clinical improvement is obtained or desired, e.g., several months or years to the remainder of the patient's life. In the case of preventing epilepsy, the total duration of therapy can be in the range of from about one day to as long as necessary to prevent development of epilepsy in the patient. Monitoring of patients for clinical improvement can be performed by conducting a procedure selected from an electroencephalogram, an evoked potential, spectral mapping, voltage mapping, clinical assessment, and combinations thereof.

As will be recognized by those of ordinary skill in the art, any or all of the foregoing vagus nerve stimulation parameters can be titrated clinically to achieve the desired response in a patient.

EXAMPLE 5

Antiepileptogenic Effect of Vagus Nerve Stimulation in a Rat Electrical Kindling Model Electrical kindling is an important model of epileptogenesis, i.e., the development of a chronic seizure focus. Since repeated kindling sessions cause progressive increases in severe seizure severity (Goddard et al. (1969) *Exp. Neurol.* 25:295–330), electrical kindling can be utilized to test for antiepileptogenic properties of a given therapy (Schmutz et al. (1988) *J. Neural. Transm.* 72:245–257; Silver et al. (1991) *Ann. Neurol.* 29:356–363). The effectiveness of vagus nerve stimulation in opposing epileptogenesis was therefore investigated using this paradigm.
Experimental Electrodes were implanted on the left vagus nerve of adult male Sprague-Dawley rats (250–300 g) to provide vagus nerve stimulation. A twisted pair depth electrode was implanted into the right amygdala (coordinates from bregma: AP −2.4mm; ventral −8.6m; lateral −4.2mm) using a stereotaxic device, and the animals were allowed to recuperate for at least one week.

Figure 4:
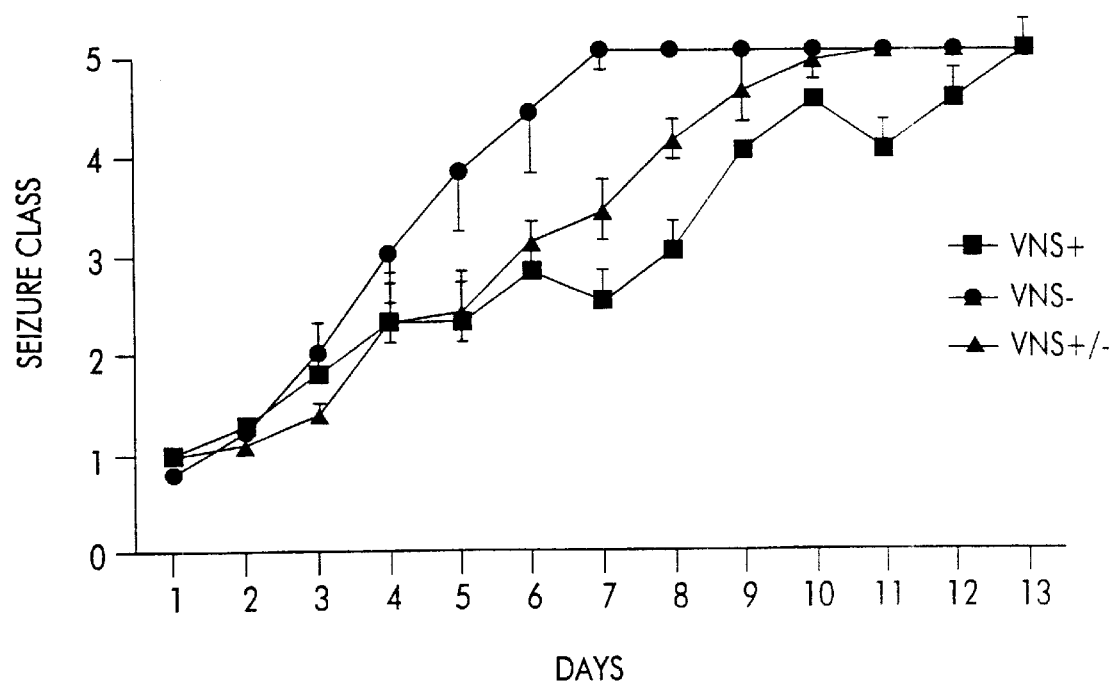
FIG. 4 is a graph showing the antiepileptogenic effect of vagus nerve stimulation in the rat electrical kindling experiment described in Example 5.

On the first day, the kindling threshold was determined by applying 100 Hz biphasic square wave pulses to the depth electrode for 30 sec. The current was increased in 10 μA increments until at least a 10 sec. aferdischarge was obtained. The resulting threshold current was recorded for each animal and used for subsequent sessions. Prior to each kindling session, vagus nerve stimulation (1 mA/30 Hz/500 μsec. biphasic square pulses) or sham stimulation (i.e., identical handling, no vagus nerve stimulation) was administered for one hour. Subsequently, daily kindling stimuli were administered through the depth electrode (biphasic square wave, 100 Hz). Seizures were scored on a standard severity scale (Racine, R. J. (1972) *Electroencephalogr. Clin. Neurophysiol.* 32:281) on a scale from 0 to 5, in which 5 represents a fully kindled convulsive seizure. The results are shown in FIG. 4.
Results As can be seen in FIG. 4, there were significant differences in the progression of kindling stage for rats that received vagus nerve stimulation pretreatment (-■-, n=4), control animals that did not receive vagus nerve stimulation (-●-, n=5), and a third comparison group (-▲-, n=7) that received vagus nerve stimulation for the first 6 days, but not for subsequent kindling sessions (p=0.0001; repeated measures ANOVA).

Post-hoc analysis revealed that there was a significant delay in animals that received vagus nerve stimulation compared to control animals (p≦0.01; Newman-Keuls test). The mean stimuli to class 5 seizures was 11.3±1.5 (days±SD) in vagus nerve stimulation-treated animals (-■-) compared to 6.0±1.2 in sham-treated animals (-●-; p=0.001; t-test).

To assure that the treatment opposed epileptogenesis rather than masking the resulting seizure, the third group received vagus nerve stimulation for 6 kindling sessions, and then received no vagus nerve stimulation during subsequent sessions. This is shown by the middle curve (-▲-) in FIG. 4. As expected, the rate of kindling in this group was similar to that in the other treated group that received the first six vagus nerve stimulations (-■-). If vagus nerve stimulation was simply masking the seizure severity, the severity score would be expected to increase to control values for the remaining kindling sessions. However, the seizure severity scores remained significantly lower than those in control animals (p≦0.01, Neuman-Keuls test), and exhibited an intermediate progression of severity increases. These results demonstrate that the vagus nerve stimulation opposed, rather than masked, epileptogenesis.

In summary, these kindling experiments indicate that vagus nerve stimulation can oppose epileptogenesis, and may therefore be a useful therapy to prevent the development of epilepsy in clinical situations associated with a high risk for developing epilepsy.

EXAMPLE 6

Treatment of Memory Disorders and Chronic Memory Impairment by Vagus Nerve Stimulation Electrical stimulation of the vagus nerve can also be used in therapies to treat subjects suffering from diseases or conditions in which memory impairment or learning disorders are a prominent feature. Examples of such diseases or conditions include Alzheimer's Disease, Binswanger Disease, Pick's Disease, Parkinson's Disease, cerebral palsy, post-meningitis, post-encephalitis, traumatic brain injury, Wernicke-Korsakoff syndrome, alcohol-related memory disorders, post-temporal lobectomy, memory loss from multi-infarct (stroke) state, multiple sclerosis, post-cardiac arrest injury, post-hypoxic injury, and near drowning.

Electrical stimulation of the vagus nerve can also be used in therapies to treat subjects suffering from disorders in which impairment of cognitive processing speed, acquisition of perceptual skills, acquisition of motor skills, or perceptual processing are a prominent feature. Examples of these diseases or conditions include mental retardation, multiple sclerosis, perinatal asphyxia, intrauterine infections, cerebral palsy, post-meningitis, post-encephalitis, dyslexia, constructional apraxia, post-cardiac arrest injury, post-hypoxic injury, multi-infarct (stroke) state, and near drowning.

Methods and Design

Apparatus

The device and electrodes can be implanted as described in U.S. Pat. Nos. 5,154,172 and 5,269,303, although any conventional devices known in the art can be employed.

Stimulation Parameters of the Output Signal

The preferred range of stimulation parameters of the output signal of the stimulus generator for the treatment of memory impairment, learning disorders, impairment of cognitive processing speed, acquisition of perceptual skills, acquisition of motor skills, or perceptual processing, and the typical value of each parameter of the output signal programmed into the device by the attending physician or therapist, can be as follows.

The pulse width can be in the range of from about 50 μsec. to about 1,500 μsec., preferably from about 100 μsec. to about 1,000 μsec., more preferably from about 250 μsec. to about 750 μsec., even more preferably from about 400 μsec. to about 750 μsec., and most preferably from about 400 μsec. to about 600 μsec. A pulse width of about 400 μsec. to about 750 μsec. is appropriate when C fiber activation is required or desired. If only A and B fiber activation is required or desired, then a pulse width of about 50 μsec. to about 250 μsec. would be effective. The type of fiber activation can vary between individual patients.

The output current can be in the range of from about 0.1 mA to about 10 mA, more preferably from about 0.1 mA to about 6 mA, most preferably from about 0.1 mA to about 4 mA.

The frequency of the output signal can be in the range of from about 1 Hz to about 75 Hz, more preferably about 5 Hz to about 60 Hz, most preferably from about 10 Hz to about 40 Hz.

The pulses can be monophasic, biphasic, or a combination thereof.

The train duration of the output current can be in the range of from about 1 sec. to about 4 hours, more preferably from about 2.5 sec. to about 2.5 hours, most preferably from about 5 sec. to about 1 hour. The interval between trains can be in the range of from about 1 sec. to about 1 week, more preferably from about 1 sec. to about 1 day, most preferably from about 5 sec. to about 4 hours. Trains can also be supplied on demand if this is determined to be preferable by the physician or therapist.

The stimulating electrical current can be applied to the vagus nerve any time after appearance of the symptom(s) to be treated.

Finally, the duration of the total therapy can vary depending upon the nature and severity of the disorder, condition, or impairment, as well as the physical attributes and condition of the patient. Therapy can vary from about one day to as long as continued clinical improvement is obtained or desired, e.g., several months or years to the remainder of the patient's life. Clinical tests that can be employed to monitor the success of therapy include standard neuropsychological tests such as WISC, WAIS, Halsted-Reitan, and combinations thereof. Useful laboratory tests include, for example, electroencephalograms, evoked potentials, spectral mapping, voltage mapping, clinical assessment, and combinations thereof.

As will be recognized by those of ordinary skill in the art, any or all of the foregoing vagus nerve stimulation parameters can be titrated clinically to achieve the desired response in a patient.

EXAMPLE 7

Treatment of Persistent Impairment of Consciousness by Vagus Nerve Stimulation

The present inventors have also concluded that vagus nerve stimulation can be employed in the treatment of persistent impairment of consciousness, such as that associated with coma or vegetative states.

Methods and Design

Apparatus

The device and electrodes can be implanted as described in U.S. Pat. Nos. 5,154,172 and 5,269,303, although any conventional devices known in the art can be employed.

Stimulation Parameters of the Output Signal

The preferred range of stimulation parameters of the output signal of the stimulus generator for the treatment of persistent impairment of consciousness, and the typical value of each parameter of the output signal programmed into the device by the attending physician or therapist, can be as follows.

The pulse width can be in the range of from about 50 μsec. to about 1,500 μsec., preferably from about 100 μsec. to about 1,000 μsec., more preferably from about 250 μsec. to about 750 μsec., even more preferably from about 400 μsec. to about 750 μsec., and most preferably from about 400 μsec. to about 600 μsec. A pulse width of about 400 μsec. to about 750 μsec. is appropriate when C fiber activation is required or desired. If only A and B fiber activation is required or desired, then a pulse width of about 50 μsec. to about 250 μsec. would be effective. The type of fiber activation can vary between individual patients.

The output current can be in the range of from about 0.1 mA to about 10 mA, more preferably from about 0.1 mA to about 6 mA, most preferably from about 0.1 mA to about 4 mA.

The frequency of the output signal can be in the range of from about 1 Hz to about 75 Hz, more preferably about 5 Hz to about 60 Hz, most preferably from about 10 Hz to about 40 Hz.

The pulses can be monophasic, biphasic, or a combination thereof.

The train duration of the output current can be in the range of from about 1 sec. to about 4 hours, more preferably from about 2.5 sec. to about 2.5 hours, most preferably from about 5 sec. to about 1 hour. The interval between trains can be in the range of from about 1 sec. to about 1 week, more preferably from about 1 sec. to about 1 day, most preferably from about 5 sec. to about 4 hours. Trains can also be supplied on demand if this is determined to be preferable by the physician or therapist.

The stimulating electrical current can be applied to the vagus nerve any time after appearance of symptoms associated with persistent impairment of consciousness, for example within a time period of from about one hour to about three months after appeance of such symptoms.

Finally, the duration of the total therapy can vary depending upon the nature and severity of the impairment, as well as the physical attributes and condition of the patient. Therapy can vary from about one day to as long as continued clinical improvement is obtained or desired, e.g., several months or years to the remainder of the patient's life.

As will be recognized by those of ordinary skill in the art, any or all of the foregoing vagus nerve stimulation parameters can be titrated clinically to achieve the desired response in a patient.

The invention being thus described, it will be obvious that the same can be varied in many ways. Such variations are not to be regarded as a departure from the spirit and scope of the present invention, and all such modifications as would be obvious to one skilled in the art are intended to be included within the scope of the following claims.

What is claimed is:

1. A method for improving learning or memory in a human or animal subject, the method comprising:
   (a) applying a stimulating electrical signal to the vagus nerve of a human or animal subject, said stimulating electrical signal being effective to enhance memory storage or consolidation processes in said human or animal subject; and
   (b) improving memory storage or improving the retention of learning experiences, in said human or animal subject.

2. A method as set forth in claim 1 further comprising producing said stimulating electrical signal with a stimulus generator implanted within said human or animal subject's body.

3. A method as set forth in claim 1 wherein the electrical signal supplies a current to the vagus nerve in the range of from about 0.1 mA to about 10 mA.

4. A method as set forth in claim 1 wherein the electrical signal supplies a current to the vagus nerve in the range of from about 0.1 mA to about 4 mA.

5. A method as set forth in claim 1 wherein the electrical signal comprises a train of pulses, each pulse having a pulse width ranging from about 50 μsec. to about 1,500 μsec.

6. A method as set forth in claim 1 wherein the electrical signal comprises a train of pulses, each pulse having a pulse width ranging from about 400 μsec. to about 750 μsec.

7. A method as set forth in claim 1 wherein the electrical signal comprises a train of pulses having a frequency ranging from about 1 Hz to about 75 Hz.

8. A method as set forth in claim 1 wherein the electrical signal comprises a train of pulses having a frequency ranging from about 10 Hz to about 40 Hz.

9. A method as set forth in claim 1 wherein the electrical signal is monophasic, biphasic, or a combination thereof.

10. A method as set forth in claim 1 wherein the electrical signal comprises a train of pulses having a train duration ranging from about 1 second to about 4 hours.

11. A method as set forth in claim 1 wherein the electrical signal comprises a train of pulses having a train duration ranging from about 5 seconds to about 1 hour.

12. A method as set forth in claim 1 wherein the electrical signal comprises trains of pulses having an interval between trains ranging from about 1 second to about 1 week.

13. A method of as set forth in claim 1 wherein the electrical signal comprises trains of pulses having an interval between trains ranging from about 5 seconds to about 4 hours.

14. A method as set forth in claim 10 wherein trains are supplied on demand.

15. A method as set forth in claim 1 further comprising monitoring said human or animal subject to determine if said learning or memory has been improved in said subject, or if further stimulation of said vagus nerve is required to improve said learning or memory in said subject.

16. A method as set forth in claim 15, wherein said monitoring is performed via a member selected from the group consisting of clinical outcome, a clinical test, a laboratory test, and combinations thereof.

17. A method as set forth in claim 15, wherein said laboratory test is selected from the group consisting of a brain scan, a PET scan, a SPECT scan, an EEG, an evoked potential, monitoring the level of a neurotransmitter in the brain, and monitoring the level of a neurotransmitter in spinal fluid.

* * * * *